United States Patent
Lipps et al.

(10) Patent No.: US 6,924,353 B2
(45) Date of Patent: Aug. 2, 2005

(54) INHIBITORS FOR RNA VIRUSES

(76) Inventors: Binie V. Lipps, 4509 Mimosa Dr., Bellaire, TX (US) 77401; Frederick W. Lipps, 4509 Mimosa Dr., Bellaire, TX (US) 77401

(*) Notice: Subject to any disclaimer, the term of this patent is extended or adjusted under 35 U.S.C. 154(b) by 35 days.

(21) Appl. No.: 10/375,310

(22) Filed: Feb. 27, 2003

(65) Prior Publication Data

US 2004/0171536 A1 Sep. 2, 2004

(51) Int. Cl.[7] ............................................. A61K 38/00
(52) U.S. Cl. .................................... 530/300; 424/185.1
(58) Field of Search ....................... 530/300; 424/185.1

(56) References Cited

PUBLICATIONS

Lipps, Binie, Isolation of subunits α, β and γ of the complex taipoxin from the venom of *Oxyuranus s. scutellatus*, Toxicon, 2000, 38:1845–1854.*

* cited by examiner

*Primary Examiner*—James Housel
*Assistant Examiner*—Stacy B. Chen

(74) *Attorney, Agent, or Firm*—John R Casperson

(57) ABSTRACT

Human immunodeficiency virus inhibiting protein (HIVIP) has been isolated from a poisonous snake, the Australian Taipan, Oxyuranus Scutellatus. HIVIP is characterized as a potent inhibitor of HIV-1 and HIV-2 viruses in cell culture. HIVIP is characterized as a stable, non toxic component of venom, having molecular weight 13,500 Daltons revealed by gel electrophoresis. The partial sequence of HIVIP for its first fifteen N-terminal amino acids is given by SEQ. ID. No: 1:

Asn Leu Ala Gln Phe Gly Phe Met Ile Arg Cys Ala Asn Gly Gly.

The active domain of HIVIP was isolated and determined to be SEQ. ID. NO.: 2:

Ala Lys Ala Gly Ser Asp Asn Thr Lys Gly Gly Val Try Pro Met Phe Gly Met.

Various peptides containing at least a portion of this sequence from the N-terminal have been shown to inhibit other RNA viruses in cell culture and are collectively termed RIPs, RNA virus Inhibitor Peptides. Such peptides can be made in abundance and cheaply to provide a synthetic therapeutic for the infections caused by RNA viruses.

15 Claims, No Drawings

SEQUENCE LISTING

```
<160> NUMBER OF SEQ ID NOS: 5

<210> SEQ ID NO 1
<211> LENGTH: 15
<212> TYPE: PRT
<213> ORGANISM: Oxyuranus scutellatus

<400> SEQUENCE: 1

Asn Leu Ala Gln Phe Gly Phe Met Ile Arg Cys Ala Asn Gly Gly
1               5                   10                  15

<210> SEQ ID NO 2
<211> LENGTH: 18
<212> TYPE: PRT
<213> ORGANISM: Oxyuranus scutellatus

<400> SEQUENCE: 2

Ala Lys Ala Gly Ser Asp Asn Thr Lys Gly Gly Val Tyr Pro Met Phe
1               5                   10                  15

Gly Met

<210> SEQ ID NO 3
<211> LENGTH: 15
<212> TYPE: PRT
<213> ORGANISM: ARTIFICIAL
<220> FEATURE:
<223> OTHER INFORMATION: SYNTHESIZED.  CORRESPONDS TO POSITIONS 1-15 OF
      SEQ. ID. NO.: 2

<400> SEQUENCE: 3

Ala Leu Ala Gly Ser Asp Asn Thr Lys Gly Gly Val Tyr Pro Met
1               5                   10                  15

<210> SEQ ID NO 4
<211> LENGTH: 10
<212> TYPE: PRT
<213> ORGANISM: ARTIFICIAL
<220> FEATURE:
<223> OTHER INFORMATION: SYNTHESIZED.  CORRESPONDS TO POSITIONS 1-10 OF
      SEQ. ID. NO.:  2

<400> SEQUENCE: 4

Ala Lys Ala Gly Ser Asp Asn Thr Lys Gly
1               5                   10

<210> SEQ ID NO 5
<211> LENGTH: 5
<212> TYPE: PRT
<213> ORGANISM: ARTIFICIAL
<220> FEATURE:
<223> OTHER INFORMATION: SYNTHESIZED.  CORRESPONDS TO POSITIONS 1-5 OF
      SEQ. ID. NO.: 2

<400> SEQUENCE: 5

Ala Lys Ala Gly Ser
1               5
```

INHIBITORS FOR RNA VIRUSES

BACKGROUND OF THE INVENTION

In one aspect, this invention relates to peptides and proteins which inhibit RNA viruses. In another aspect, this invention relates to the use of such peptides and proteins to inhibit RNA viruses in humans.

Bishop et al (1) discovered rotavirus, a double stranded RNA virus, as a human pathogen in 1973. The virus causes diarrheal disease, especially in children and until today, there is no specific treatment. Rotavirus is implicated in infant diarrhea and the disease has great impact in developing countries. The burden of rotavirus diarrhea in the United States for ages 1 to 4 is estimated to include over one million cases of severe diarrhea and up to 150 deaths per year. (Ho et al (2)). In vitro suppression of rotavirus using a purified fraction of bovine lecithin has been reported. Smee et al (3) reported the inhibition of rotavirus by selected antiviral substances. Passive protection of neonates against rotavirus associated gastrointestinal symptoms in a nursery was observed following the oral administration of human gamma globulin containing rotavirus antibodies (Barnes et al (4)) Currently, there is no vaccine for preventive measure.

The paramyxoviruses are single stranded RNA viruses include the most important agents of respiratory infections of infants and children. Those are respiratory syncytial virus (RSV) and parainfluenza virus (PIV). RSV has been recognized as a leading cause of serious lower respiratory tract infections in infants and children under age 2 years (Parrott et al (5) and lower respiratory tract infections in adults (Dowell et al (6)). No vaccine is currently available to prevent RSV infections and the utilization of ribavirin, the only approved drug to treat RSV infections, is controversial. (Committee on Infectious Diseases (7)).

Parainfluenza viruses are ubiquitous and cause common respiratory illnesses in persons of all ages referred to as "common cold syndrome." Wilson et al. (8) studied the use of amantadine and ribavirin as aerosol treatment for influenza A and B virus infections in mice. Gilbert et al (9) further studied the short duration of ribavirin aerosol for the treatment of influenza virus in mice and RSV infections in cotton rats. None of these drugs became commercially available for humans.

The causative agent of Acquired Immunodeficiency Syndrome (AIDS) has been identified as Human Immunodeficiency Virus, HIV. (Gallo et al (10)). The search for new and effective agents for the treatment of HIV infection continues. The following four approved antiviral drugs for the treatment of AIDS, AZT, DDI, DDC and D4T, work by blocking the viral enzyme, reverse transcriptase (Connolly et al (11)). The replication of HIV also requires another enzyme, the HIV protease (PR). A variety of successful PR inhibitors have been discovered which inhibit the replication of HIV in cell cultures (Drake et al (12)). A number of structurally diverse derivatives have been reported to inhibit the replication and cytopathic effects of the HIV in cell cultures. These include linear peptides (Frechet et al (13)), cyclic metabolites (Nakashima et al (14)) and peptide mimetic enzyme inhibitors (Gustafson et al (15)). Some of them are in use for treatment of AIDS with border-line efficacy.

Snake venom is a complex mixture of numerous bioreactive components, such as toxins, enzymes, hormones, activators, inhibitors and growth factors with a wide spectrum of biological activities. The anticoagulant, Ancrode, is the only venom-derived protein in use for human therapeutics. However, snake venoms or purified proteins from venoms were used for inhibition of polio and semiliki viruses in cell cultures and animals. It was also observed (Anderson et al (16)) that 100 $\mu$g/ml of purified phospholipase $A_2$ (PLA2) from Pseudechis porphyriacus venom, rapidly decreased the infectivity titer of Murray valley encephalitis virus. It was also reported (Wahlstrom (17)) that PLA2 from Naja nigricolis venom partially disrupted the envelop of influenza virus. It is clear from the literature that snake venom proteins were tested for their antiviral properties two decades ago.

However, a therapeutic material to treat RNA virus infections in humans remains very desirable.

(1) Bishop, R. F., Davidson, G. P., Holmes, I. H., Ruck, B. J. Virus particles in the epithelial cells of duodenal mucosa from children with acute non-bacterial gastroenteritis. Lancet 2, 1281–1283 (1973).

(2) Ho, M. S., Glass, R. I., Pinsky, R. F., Anderson, L. L. Rotavirus as a cause of diarrheal morbidity and mortality in the United States. J. Infect. Dis. 158, 1112–1116 (1988).

(3) Smee, D. F., Sidwell, R. W., Clark, S. M., Barnett, B. B., Spendlove, R. S. Inhibition of rotaviruses by selected antiviral substances: mechanism of viral inhibition and in vivo activity. Antimicrob. Agents Chemother 21, 66–73 (1982).

(4) Barnes, G. L., Doyle, L. W., Hewson, P. H., Knoches, A. M. L., McClellan, J. A., Kitchen, W. H., Bishop, R. H. 1982. A randomised trial of oral gamma globulin in low-birth weight infants infected with rotavirus. Lancet 1, 1371–1373 (1982).

(5) Parrott, R. H., Kim, H. W., Arrobio, J. O., Hodes, D. S., Murphy, B. R., Brand, C. D., Camargo, E. Chanock, C. M. 1973. Epidemiology of respiratory syncytial virus infection in Washington, DC. Am. J. Epidemiol. 98, 289–300 (1973).

(6) Dowell, S. F., Anderson, L. J., Gary, H. E. Jr., Erdman, D. D.,Plouffe, J. F., File, T. M. Jr., Marston, B. J., Breiman, R. F. Respiratory syncytial virus is an important cause of community-acquired lower respiratory infection among hospitalized adults. J. Infect. Dis. 174, 456–462 (1996).

(7) Committee on Infectious Diseases, Use of ribavirin in the treatment of respiratory syncytial virus in infection. Pediatrics 92, 501–504 (1993).

(8) Wilson, S. Z., Knight, V., Wyde, P. R., Drake, S., Couch, R. B., Amantadine and ribavirin aerosol treatment of influenza A and B infection in mice. Antimicrob. Agents Chemother. 17, 642–648 (1980).

(9) Gilbert, B. E., Wyde, P. R., Ambrose, M. W., Wilson, S. Z., Knight, V., Further studies with short duration ribavirin aerosol for the treatment of influenza virus infection in mice and respiratory syncytial virus in cotton rats. Antivir. Res. 17, 33–42 (1992).

(10) Gallo, R., Sarin, P. S., Gelmann, E. P., Robert-Guroff, M., Richardson, R., Kalyanaraman, V. S., Mann, D., Sidhu, G. D., Stahl, R. E., Zolla-Pazner, S., Leibowitch, J. Popovic M., Isolation of human T-cell leukemia virus in acquired immune deficiency syndrome (AIDS), Science 220, 865–867 (1983).

(11) Connolly, K. J., Hammer, S. C., Antiviral therapy: Reverse transcriptase inhibition. Antimicrobial Agents and Chemotherapy, 36, 245–254 (1992).

(12) Drake, P. L., Huff, J. R. 1994. HIV protease as an inhibitor target for the treatment of AIDS. Advances in Pharmacology, 25, 399–453 (1994).

(13) Frechet, D., Guitton, J. D., Herman, F., Faucher, G., Helynck, B. Monegier du Sorbier, Ridoux, J. P., James- Surcouf, E., Vuilhorgne, M. Solution structure of RP 71955, a new amino acid tricyclic peptide active against HIV-1 virus. Biochemistry 33: 42–50 (1994).

(14) Nakashima, H., Masuda, M., Murakami, T., Koyanagi, T., Matsumoto, A., Fujii, N., Yamamoto, N. Anti-human immunodeficiency virus activity of a novel synthetic peptide, T22 (Tyr-5, 12, Lys-7) polyphemusin II): a possible inhibitor of virus cell fusion. Antimicro. Agents Chemother. 36, 1249–1255 (1992).

(15) Gustafson, K. R., Sowder II, R. C., Henderson, L. E., Parsons, I. C., Kashman, Y., Cardellina, J. H., McMahon, J. B., Buckheit Jr., R. W., Parnell, L. K., Boyd, M. R. Circulins A and B: Novel HIVinhibitory microcyclic peptides from the tropical tree Chasalia parvifolia. J. Am. Chem. Soc. 116, 9337–9338 (1994).

(16) Anderson, S. G., Ada, G. L.. A lipid component of Murray Valley encephalitis virus. Nature (London) 188: 876–880 (1960).

(17) Wahlstrom, A. Purification and characterization of PhLA2 from the venom of *Naja nigricolis*. Toxicon 9, 45–56 (1971).

SUMMARY OF THE INVENTION

In one aspect, the invention provides a method for treating a condition caused by an RNA virus in humans. The method is carried out by identifying a patient suffering from a condition caused by an RNA virus, and then administering to the patient an amount of a compound composed of an amino acid chain which is effective to inhibit the replication of the RNA virus. The amino acid chain contains SEQ. ID. NO.: 5.

In another embodiment of the invention, there is provided a composition of matter having antiviral activity consisting essentially of a peptide containing no more than 25 amino acids total and SEQ. ID. NO.: 5.

DETAILED DESCRIPTION OF THE INVENTION

An inhibitor to human immunodeficiency virus (HIV), having molecular weight 13.5 kDa was isolated from the venom of Australian Taipan snake *Oxuranus s. Scutellatus*. We named this protein HIVIP, which is the acronym for Human Immunodeficiency Virus Inhibitor Protein. The active domain of HIVIP was subsequently identified and has been synthesized. We have named this peptide RIP, the acronym for RNA virus Inhibitor Peptide, because of its ability to inhibit the infectivity of other RNA viruses. HIVIP is occasionally referred to herein as natural RIP.

Selection of Candidate Venom

Initially, in search of potential HIV inhibitory component/s crude venoms from snakes belonging to the families Crotalidae, Elapidae and Viperidae were tested by the National Institute of Health (NIH), AIDS Drug Screening and Development Laboratory. It was revealed that the venoms from two species of snakes, namely: *Oxyuranus scutellatus*, of the Elapidae family; and *Vipera russelli*, of the Viperidae family showed HIV inhibition in cell cultures. Furthermore, the concentration of *O. scutellatus* venom causing inhibition of HIV was not toxic to the normal cells, whereas the concentration of venom of *V. russelli* was toxic to both normal and the HIV infected cells. Therefore, venom of *O. scutellatus* was selected for further study and was separated into components, which were provided to NCI Anti-AIDS Virus Drug Screening Laboratory for further testing.

Isolation of HIVIP

Human Immunodeficiency Virus Inhibiting Protein (HIVIP) was isolated from the venom of a poisonous snake, the Australian Taipan, *Oxyuranus Scutellatus*. MVIP is characterized as a potent inhibitor of HIV-1 and HV-2 viruses in cell cultures. The concentration of HIVIP as low as 5 nanogram/ml inhibits the replication of HIV viruses in CEM and MT-4, CD4+ cells. Furthermore, HIVIP inhibits the replication of HIV strains which are resistant to AZT, the first approved drug. HIVIP is non toxic to the normal cells in concentrations up to $100 \mu g/ml$. HIVIP is characterized as a stable, non toxic component of venom, having a molecular weight 13,500 Daltons as revealed by gel electrophoresis. The partial sequence of HIVIP for its first fifteen amino acids from the N-terminal matches exactly the phospholipase A2 from Taipan venom and it is similar to the phospholipases of other snake species. However, these other phospholipases do not show HIV inhibitory activity. Hence this particular protein is of special value.

Human Immunodeficiency virus inhibiting protein HIVIP consists essentially of a peptide containing the partial amino acid sequence:

Asn Leu Ala Gln Phe Gly Phe Met Ile Arg Cys Ala Asn Gly Gly (SEQ. ID. NO.: 1).

Preferably, the peptide HIVIP contains SEQ. ID NO: 1 beginning at its N-terminal. More preferably, the peptide HIVIP has a molecular weight of about 13,500 Daltons, which can be revealed by electrophoresis. In addition, HIVIP is stable at 4° C. storage, which maintains its biological activity. HIVIP is also stable at room temperature, 74° F., for at least several weeks.

HIVIP may be obtained essentially as a fraction of venom, from any subspecies of poisonous Taipan snakes. HIVIP is preferably obtained from the venom of a species of *O. Scutellatus*, the Australian Taipan snake.

HIVIP may be obtained by separating the proper active peptide fraction from the venom using gel filtration chromatography, electrophoresis, high pressure liquid chromatography, ion exchange chromatography or a combination thereof.

Fractionation of Venom: HIVIP is preferably separated from fresh liquid venom, although lyophilized whole venom may also be used. The liquid venom is diluted 1:4 with 0.01 M phosphate buffer saline (PBS) and preferably centrifuged to sediment insoluble debris, which can also be removed by filtration. Approximately 40 mg venom is fractionated on high pressure liquid chromatography, from Toso Co. Japan and the anion exchange column from Polymer Laboratories UK, maintained at 20° C. temperature. A plurality of fractions are eluted according to relative ionic charge, preferably using gradient Trizma-HCl buffer at pH 7.3. The Toso high pressure liquid chromatography automatically mixes water and 1.0 molar Trizma-HCl buffer to yield gradient Trizma-HCl buffer in the range 0.01 molar to 1.0 molar. Any suitable gradient buffer can be used with pH in the range 6.0 to 8.0.

The venom of *O. Scutellatus* resolved into 11 major fractions by high pressure liquid chromatography. Each fraction was collected and dialyzed against water using a dialysis apparatus from the Spectrum Co. and the protein concentration was adjusted to $100 \mu g/ml$. All 11 fractions were tested individually by NCI for HIV inhibitory activity in cell cultures. Under the procedure used, the first two eluted fractions were found to contain active HIV inhibitor. The fraction containing the anti HIV active peptide may be used in this form as a HIV inhibitor, but, preferably, it is further purified to 100% purity to completely remove any inactive substances. Preferably, the anti HIV active fractions 1+2 are concentrated and dialyzed simultaneously, to $\frac{1}{20}^{th}$ volume and then re-purified by high pressure liquid chromatography by a second run under identical conditions of gradient buffer, temperature, etc. Under these conditions, fractions 1+2 were resolved into a single peak.

The material from the second passage, which is pure HIVIP, showing one band corresponding to a material having a molecular weight of approximately 13,500 Daltons as revealed by electrophoresis using known molecular weight markers. The 100% pure material of HIVIP was sequenced for the first fifteen amino acids from the N-terminal and the result is given by SEQ. ID NO: 1:

Asn Leu Ala Gln Phe Gly Phe Met Ile Arg Cys Ala Asn Gly Gly.

A PIR data bank search revealed an exact match with Accession# S21101;

Title: Phospholipase A2—Australian Taipan EC# 3.1.1.4;

Source: *Oxyuranus Scutellatus* #common name: Australian Taipan.

Initially, all venom fractions were tested by NCI for HIV inhibiting activity on CEM and MT-4 cells in concentrations ranging from 5 μg/ml down to 0.1 μg/ml. The inhibitory pattern of cells in presence of each fraction was compared to the control cells. The fractions 1 and 2 of *O. Scutellatus* venom showed the most inhibitory activity on CEM and MT-4 cells at lower than 0.1 μg/ml concentration.

The pool of fractions 1 and 2 was concentrated and refractionated on HPLC under identical conditions to obtain 100% pure HIVIP. Then NCI tested extensively the 100% pure HIVIP and concluded that HIVIP is a potent HIV inhibitor down to a concentration of $6 \times 10^{-3}$ μg/ml. The results in tabular form provided by the Anti-AIDS Virus Drug Screening Laboratory NCI-FCRDC are shown in Table 1.

TABLE 1

Inhibition of p24 ($IC_{50}$) synthesis in monocyte/macrophages at a concentration of 10 μg/ml natural RIP

| | HIV strains | | | | | | | |
|---|---|---|---|---|---|---|---|---|
| | $HIV_{RF}$ | A17 | N19 | DPS | AZTsen | AZTres | $HIV-2_{ROD}$ | SIV |
| EC5m0 | 0.02 | 45.5 | 25.8 | 6.04 | 105 | 38.2 | <.05 | 99.1 |
| IC50 | 63.0 | 113 | 133 | >162 | >162 | 72.2 | 57.6 | >162 |
| TI | 3150 | 2.48 | 5.16 | >26.9 | >1.54 | 1.88 | <1150 | >1.64 |

The results in Table 1 obtained from NCI clearly showed that natural RIP (HIVIP) is a potent inhibitor of p24 of various types of strains of HIV. p24 is a core protein of HIV and the replication of the virus cannot proceed without p24. The inhibitory activity of HIVIP is greater in CEM cells than in MT-4 cells for reasons not presently understood. HIVIP is also capable of inhibiting the virus replication of HIV strains resistant to the AZT drug. Thus RIP is a potent inhibitor for HIV replication, and may become a candidate for AIDS therapy. RIP is non-toxic to uninfected cells up to 50 μg/ml.

Clinical Tests for Side Effects:

HIVIP was tested for side effects in human AIDS patients. One milligram of HIVIP in four milliliters fluid was administered intravenously to the patients by practicing physicians, one in Houston, one in Thailand, and two in Russia. None of the patients showed any side effects after observation for two months.

Inhibition of infectivity of rotavirus SA 11 strain in presence of various concentrations of natural RIP: The monolayers of MA 104 cells were made in 48 well plate. The monolayers were washed with serum free medium. The cells were infected with SA 11, from $10^{-2}$ to $10^{-8}$ virus dilutions made in serum free medium. Five wells were used for each concentration of the virus. The serum free special medium containing 1 μg/ml trypsin was used throughout the experiments for infected and control uninfected cells. The virus was allowed to absorb for one hour at 37° C. in humid $CO_2$ incubator after which 0.9 ml medium plus 100 μl containing various concentrations; 20 μg, 10 μg, 5 μg and 2.5 μg of RIP were added. The same concentrations of RIP were added to the uninfected controls. The positive control wells received 100 μl of PBS. The test results were read after six days for cytopathic effects (CPE). The CPE titers were expressed as tissue culture infectivity dose ($TCID_{50}$/ml) of average of five. Results are shown in Table 2.

TABLE 2

Dose dependent inhibition of infectivity of SA 11 virus in presence of natural RIP in MA 104 cells.

| | Log $TCID_{50}$ of SA 11 virus | |
|---|---|---|
| Additive | Before absorption of virus | After absorption of virus |
| PBS | 7.7 | 7.8 |
| 20 μg/ml RIP | 4.1 | 4.3 |
| 10 μg/ml RIP | 4.0 | 4.1 |
| 5 μg/ml RIP | 4.2 | 4.5 |
| 2.5 μg/ml RIP | 4.7 | 5.0 |

Table 2 shows that natural RIP inhibited SA 11 virus in MA 104 cells whether it was added before or after the virus absorption. The optimum concentration of RIP was 10 μg/ml, where inhibition of the virus was the highest. RIP proved to be a potent inhibitor of SA 11 causing three to four logs of inhibition at 10 μg/ml concentration. Uninfected MA 104 cells in the presence of up to 200 μg/ml of RIP were not affected.

Kinetics of Replication of SA 11 Virus in MA Cells in the presence of 10 μg/ml RIP:

Monolayers of MA 104 cells in 25 cm flasks were infected with SA 11 at $10^{-2}$ dilution. RIP was added to the medium to yield 10 μg/ml and an equivalent amount of PBS was added for the control medium. Half number of the flasks received 4.0 ml medium containing 40 μg of RIP corresponding to 10 μg/ml and the remaining half received medium containing PBS. Two flasks from each category were harvested by freezing and thawing once, after 2, 4, 6 and 8 days of incubation The harvests were assayed for infectivity titers in MA 104 cells. Results are shown in Table 3.

TABLE 3

Kinetics of replication of SA 11 virus in MA 104 cells in presence of 10 μg/ml natural RIP

| | Log TCID$_{50}$ of SA 11 virus | | |
|---|---|---|---|
| Harvest Period | Medium + PBS | Medium + 10 μg/ml RIP | Log Inhibition of infectivity |
| 2 D | 6.5 | 3.1 | 3.4 |
| 4 D | 6.7 | 4.0 | 2.7 |
| 6 D | 7.1 | 4.2 | 2.9 |
| 8 D | 6.9 | 4.2 | 4.7 |

Table 3 shows that the replication of SA 11 virus is inhibited from the beginning of the infection in the presence of natural RIP. The virus yield in the presence of RIP was lower by three to four logs in comparison to the controls. The results emphasized that the snake venom derived natural RIP proved to be a potent inhibitor for SA 11 in MA 104 cells.

Inhibition of infectivity of RSV and PIV3 viruses in presence of 10 μg/ml of RIP: The monolayers of HEp cells were made in 48 well plates. After pilot titrations of the virus stock, the cells were infected with RSV virus (respiratory syncytial virus) from $10^{-1}$ to $10^{-6}$, and PIV3 virus (paramyxovirus human parainfluenza type 3) from $10^{-2}$ to $10^{-8}$. Three wells were used per dilution of the virus. The medium containing 2% serum was used to make virus dilutions and for maintaining the cultures after infection. The virus was allowed to absorb for 1 hr and 0.9 ml medium containing PBS for the controls and 10 $\mu$g/ml RIP was added per well to the infected and non-infected cells. The tests were read after six days. Results are shown in Table 4.

TABLE 4

| Inhibition of infectivity of RSV and PIV3 viruses in presence of 10 $\mu$g/ml natural RIP in medium containing 2% serum. | | | |
|---|---|---|---|
| | Log $TCID_{50}$ of RSV and PIV3 viruses | | |
| Virus | Medium + PBS | Medium + 10 $\mu$g/ml RIP | Log inhibition of infectivity |
| RSV | 6.2 | 4.1 | 2.1 |
| PIV3 | 7.8 | 5.5 | 3.3 |

Table 4 shows that RIP at the concentration of 10 $\mu$g/ml inhibited the infectivity of RSV and PIV3 viruses by two to three logs in HEp2-cells. Uninfected HEp2 cells in the presence of up to 200 $\mu$g/ml of RIP in medium containing 2% serum were not affected.

Identification of the Active Domain of HIVIP by Trypsin Digestion: Purified homogeneous preparation of HIVIP was treated with trypsin dissolved in 0.1 M ammonium bicarbonate buffer pH 8.0. HIVIP and trypsin were mixed in 40:1 ratio, precisely 5 mg of HIVIP to 0.25 mg trypsin. The mixture was incubated at 37° C. to cause fragmentation at arginine and lysine sites. After 18 hours of incubation the reaction was stopped by cooling the mixture at 4° C.

Separation of Fragments from Trypsin Digest: The trypsin-digested fragments were separated on HPLC. Trypsin digested HIVIP resolved into eight different fragments. The fragments were collected individually and were dialyzed against water using 500 Daltons weight cutoff tubing (Spectrum USA). The protein concentration of each fragment was measured by using A Bio-Rad (USA) protein kit and the concentration of each fragment was adjusted to 100 $\mu$g/ml in 0.05 M phosphate buffered saline (PBS).

Biological Activity of Fragments: Initially, the inhibitory activity of the fragments was tested on African green monkey kidney cells MA104 infected with rotavirus strain SA 11. Dulbecco Modified Eagle's Medium (DMEM) containing 10% newborn calf serum (NBCS), L-glutamine and the antibiotics penicillin and streptomycin was used to grow MA 104 and HEp2 cells into monolayers after being monodispersed with a mixture of trypsin/EDTA. The same medium without serum, containing 1 $\mu$g/ml trypsin, designated as "special medium," was used after infecting MA 104 cells with SA 11 virus including the controls. Initially, each fraction was tested on monolayers of MA 104 cells grown in 48 well plates and infected at $10^{-2}$ dilution of SA 11 virus. Before infecting, MA 104 cells were washed with serum free medium. The virus was allowed to absorb for 1 hour at 37° C. in a humid $CO_2$ incubator. After absorption, 0.9 ml of medium was added to each well. Each fraction was tested at the concentration of 20, 10, 5, 2.5, and 1.0 $\mu$g/ml. Cells infected with virus received PBS to serve as positive controls, for virus CPE. The tests were read after six days. It was revealed that one of the fragments showed the highest inhibition of rotavirus virus was considered as RNA virus Inhibitor (RIP).

Synthesis of RIP: On sequencing it was found that the most active fragment of natural RIP consisted of 18 amino acids,

```
SEQ ID. NO.: 2:
A K A G S D N T K G G V Y P M F G M;

Ala-Lys-Ala-Gly-Ser-Asp-Asn-Thr-Lys-Gly-Gly-Val-

Tyr-Pro-Met-Phe-Gly-Met.
```

Three different synthetic versions were made having 15, 10 and 5 amino acids from the N-terminal:

```
SEQ. ID. NO.: 3
A K A G S D N T K G G V Y P M
``` for 15 amino acids;

```
SEQ ID. NO.: 4
A K A G S D N T K G
``` for 10 amino acids; and

```
SEQ. ID. NO.: 5
A K A G S
``` for five amino acids.

All versions displayed some antiviral activity. We found that the synthetic peptide consisting of 10 amino acids exhibited the most inhibition to rotavirus. The sequencing and synthesis was contracted out to the Protein Core Laboratory of Baylor College of Medicine, Houston, Tex. The sequence for the most active synthetic version of RIP from N-terminal was found to be A K A G S D N T K G; Ala-Lys-Ala-Gly-Ser-Asp-Asn-Thr-Lys-Gly (SEQ. ID. No.: 4).

Infectivity Inhibition of RNA Viruses by Synthetic RIP: For comparison, the natural and the synthetic RIPs were tested in cell cultures infected with different RNA viruses. The cell line MA 104 was used for infecting rotavirus SA 11 strain. HEp2 cells were used for infecting RSV and PIV3 viruses. The cells were infected in serial dilutions from $10^{-2}$ to $10^{-8}$; three wells were used for each dilution. After absorption of the virus, the cultures were divided into three groups. Group one received medium containing PBS as a positive control, group two received medium containing 10 μg/ml of natural RIP, and for the remaining group the medium was incorporated with 10 μg/ml synthetic RIP. The tests were read after six days and TCID/50 were calculated from CPE. The results are seen in Table 5.

TABLE 5

Log Inhibition of infectivity in the presence of Natural RIP and Synthetic RIP at the concentration of 10 μg/ml

| Virus | Cell Line | Additive | Log $TCID_{50}$ | Nat RIP | Syn RIP |
| --- | --- | --- | --- | --- | --- |
| Rotavirus | MA 104 | PBS | 6.2 | | |
| | | Nat RIP | 4.1 | 2.1 | |
| | | Syn RIP | 4.3 | | 1.9 |
| RSV | Hep2 | PBS | 6.2 | | |
| | | Nat RIP | 4.1 | 2.1 | |
| | | Syn RIP | 4.5 | | 1.7 |
| PIV3 | Hep2 | PBS | 7.8 | | |
| | | Nat RIP | 5.5 | 2.3 | |
| | | Syn RIP | 5.8 | | 2.0 |

Table 5 clearly shows the inhibition of infectivity of rotavirus, RSV and PIV3 viruses in the presence of synthetic RIP was comparable to that of the natural RIP. Log TCID/50 for rotavirus was 6.2 and with natural RIP and synthetic RIP were 4.1 and 4.5 respectively, giving the log TCID/50 infectivity inhibition 2.1 and 1.9 respectively.

The approved drug ribovirin was tested for RSV virus in HEp2 cells at 10 μg/ml concentration. The results showed that log TCID/50 for RSV with ribovirin was 5.4, with natural RIP yielding 5.5 and synthetic RIP yielding 5.8. Thus the reduction in infectivity for RSV provided by synthetic RIP at 10 μg/ml concentration was comparable to that provided by ribovirin. Synthetic RIP should be more inhibitory by increasing the concentration.

Discussion: Currently, there is no specific treatment or vaccine for the diseases caused by RNA viruses, such as diarrhea in children, influenza and lower respiratory tract infections in children and adults. Synthetic RIP can be given orally for diarrhea caused by rotavirus and by nasal spray for the infections caused by RSV and influenza viruses. It can be administered by oral or subcutaneous injections for AIDS.

We thus view one aspect of our broad invention as a method for treating a condition caused by an RNA virus in humans. The method is carried out by identifying a patient suffering from a condition caused by an RNA virus. The identification of such a patient can be accomplished using known techniques. There is then administered to the patient an amount of a compound composed of an amino acid chain which is effective to inhibit the replication of the RNA virus. The amino acid chain contains SEQ. ID. NO.: 5.

In one embodiment, the amino acid chain contains SEQ. ID. NO.: 1 beginning at its N-terminal. Further, the amino acid chain can form a protein having a molecular weight of about 13,500 Daltons. Still further, the protein can be isolated from the venom of *Oxyuranus Scutellatus*, such as by techniques shown hereinabove. The protein is administered in a manner to reach the blood stream of the patient.

Generally speaking the protein is administered in an amount of from about 0.01 to about 100 milligrams daily, preferably in an amount of from about 0.1 to about 10 milligrams daily. It can be suitably administered intravenously after being dispersed in a fluid. An amount in the range of 0.02 to 2 milligrams daily is also believed suitable. It is believed that the protein will be effective when administered so as to result in a concentration in the patient of between 1 and 100 ppb. Functionally phrased, the protein is administered in an amount sufficient to result in a concentration of the protein in the patient which high enough to inhibit the replication of RNA virus but beneath a concentration which is toxic to normal cells. It may be necessary to temporarily discontinue the administration of the protein in the event of antibody-forming reaction in the patient. In such event, the administration is repeated after the passage of a sufficiently long period of time to eliminate the antibodies to the protein.

It is believed that the invention will be effective to inhibit replication of RNA viruses selected from the group consisting of rotavirus, paramyxovirus, and Human Immunodeficiency Virus.

Examples of paramyxovirus are syncytial virus and parainfluenza virus. Examples of Human Immunodeficiency Viruses are HIV-1 and HIV-2.

In another embodiment, the amino acid chain forms a peptide containing in the range of from 5 to 25 amino acids and the peptide is administered in a manner to reach the blood stream of the patient. Alternative effective methods of administering such peptides are available and the risk of antibody reaction is lower. Preferably, the peptide contains in the range of 5 to 20 amino acids and is capable of crossing the blood-brain barrier. More preferably, the peptide is administered by an administration technique selected from the group consisting of nasal insulation, buccal administration, oral ingestion, intramuscular injection and subcutaneous injection.

In a further preferred embodiment, the peptide contains SEQ. ID. NO.: 4, which was found to be the most active domain. Peptides containing SEQ. ID. NO.: 3 and SEQ. ID. NO.: 2 were also effective. Most preferably, the peptides contain the given SEQ. IDs beginning at their N-terminal, because these material were tested and proved to be active.

Peptides containing in the range of 5 to 15 amino acids are expected to be highly useful when administered in the amounts as stated above for the protein.

The class of peptides provided in accordance with the invention can be characterized as compositions of matter consisting essentially of a peptide containing no more than 25 amino acids total and SEQ. ID. NO.: 5. Peptides further containing SEQ. ID. NO. 4, SEQ. ID. NO.: 3, and SEQ. ID. NO.: 2 are also considered to be within the scope of the invention. The preferred compositions contain the sequence given by the SEQ. ID. Nos. beginning at their N-terminals, and more preferably contain contain in the range of 5 to 18 amino acids. The most preferred peptides are those consisting essentially of SEQ. ID. Nos. 2, 3, 4 and 5 because these compositions were tested with good results.

While certain preferred embodiments of the invention have been described herein, the invention is not to be construed as being so limited, except to the extent that such limitations are found in the claims.

What is claimed is:

1. A composition of matter consisting essentially of a peptide containing no more than 25 amino acids total, said peptide including and SEQ. ID. NO.: 5.

2. A composition of matter as in claim 1, said peptide including SEQ. ID. NO. 4.

3. A composition of matter as in claim 1, said peptide including SEQ. ID. NO.: 3.

4. A composition of matter as in claim 1, said peptide including SEQ. ID. NO.: 2.

5. A composition of matter as in claim 1 wherein SEQ. ID. NO.: 5 is positioned at the N-terminal.

6. A composition of matter as in claim 1 wherein SEQ. ID. NO.: 4 is positioned at the N-terminal.

7. A composition of matter as in claim 1 wherein SEQ. ID. NO.: 3 is positioned at the N-terminal.

8. A composition of matter as in claim 1 wherein SEQ. ID. NO.: 2 is positioned at the N-terminal.

9. A composition of matter as in claim 1 wherein said peptide contains in the range of 5 to 18 amino acids.

10. A composition of matter as in claim 9 wherein said peptide includes SEQ. ID. NO. 4.

11. A composition of matter as in claim 9 wherein said peptide includes SEQ. ID. NO.: 3.

12. A composition of matter as in claim 9 wherein said peptide includes SEQ. ID. NO.: 2.

13. A composition of matter as in claim 9 wherein SEQ. ID. NO.: 4 is positioned at the N-terminal.

14. A composition of matter as in claim 9 wherein SEQ. ID. NO.: 3 is positioned at the N-terminal.

15. A composition of matter as in claim 13 consisting essentially of SEQ. ID. NO.: 4.

* * * * *